United States Patent [19]

Shroff et al.

[11] Patent Number: 4,478,834

[45] Date of Patent: Oct. 23, 1984

[54] DIHYDROPYRIDINES AND THEIR USE IN THE TREATMENT OF ASTHMA

[75] Inventors: James R. Shroff, Riverside, Conn.; Bernard Loev, Scarsdale, N.Y.

[73] Assignee: USV Pharmaceutical Corporation, Tarrytown, N.Y.

[21] Appl. No.: 465,849

[22] Filed: Feb. 11, 1983

[51] Int. Cl.$^3$ .................... A61K 31/44; C07D 471/04; C07D 491/052; C07D 495/04
[52] U.S. Cl. .............................. 424/246; 424/248.51; 424/248.52; 424/248.53; 424/248.54; 424/248.55; 424/250; 424/256; 424/258; 544/58.6; 544/126; 544/361; 546/80; 546/81; 546/88; 546/89; 546/92

[58] Field of Search ...................... 546/80, 81, 88, 89, 546/92; 544/58.6, 126, 361; 424/246, 248.51, 248.52, 248.53, 248.54, 248.55, 250, 256, 258

[56] References Cited

U.S. PATENT DOCUMENTS 3,689,497 9/1972 Brown et al. ...................... 546/89 X
3,991,064 11/1976 Brown et al. ......................... 546/81

OTHER PUBLICATIONS

Kametani et al., J. Chem. Soc. C., vol. 12, (1969), pp. 1616-1619.
Kametani et al., Chemical Abstracts, vol. 71, (1969), 70520j.

Primary Examiner—Richard L. Raymond

[57] ABSTRACT

New dihydropyridines are described. These compounds are useful in the treatment of asthma.

18 Claims, No Drawings

DIHYDROPYRIDINES AND THEIR USE IN THE TREATMENT OF ASTHMA

DESCRIPTION OF THE INVENTION

This invention relates to new anti-allergy agents and more particularly to certain dihydropyridines having anti-allergy activity of particular use in the treatment of asthma.

The dihydropyridines of this invention are represented by the following formula:

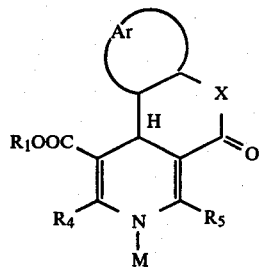

and pharmaceutically acceptable salts thereof, wherein:

Ar is phenyl, naphthyl, heteroaryl and, phenyl mono- or disubstituted by halo, $CF_3$, $NO_2$, COOH, COOR, CN, lower alkyl S, lower alkyl SO, lower alkyl $SO_2$, $OCF_3$, $SCF_3$, $OC \equiv CH$, $OCH_2CH-CH$, $CONH_2$, $=C=CH-$ lower alkyl, lower aralkyl, styrryl, lower cycloalkyl having 5 to 7 carbons;

X is S, NH, O, or N—R;

$R_1$ is H, lower alkyl, aralkyl, aminoalkyl, dialkylamino, aralkylamino phenylthio, phenyl sulfoxide, phenyl sulfone, alkoxyalkyl, hydroxyalkyl, alkenyl, cycloalkyl or aryl;

$R_4$ and $R_5$ are independently lower alkyl, formyl, CN, $CH_2OH$, dialkylaminomethyl, dialkylaminoethyl,

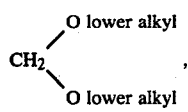

aryl, aryl lower alkyl,

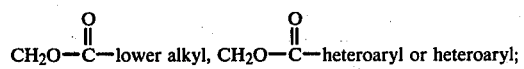

$CH_2O-\overset{O}{\underset{\|}{C}}-$lower alkyl, $CH_2O-\overset{O}{\underset{\|}{C}}-$heteroaryl or heteroaryl;

M is H, alkyl, aryl, alkoxy, $(CH_2)_nCOOR$,

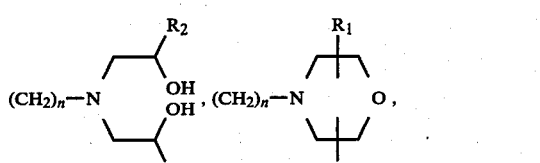

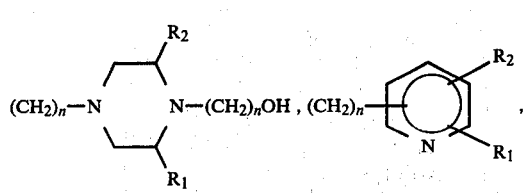

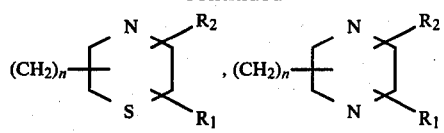

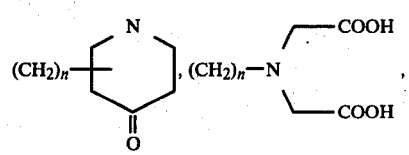

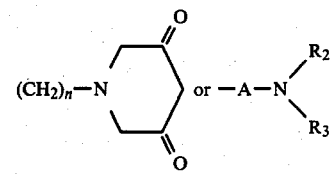

wherein
A is $C_2$ to $C_4$ alkyl and may be branched or straight, R is H or lower alkyl, $R_2$ and $R_3$ are independently H, lower alkyl, phenyl or phenyl lower alkyl, and n is 0–2 inclusive useful in the treatment of asthma.

The alkyl group in aralkyl, amino alkyl, aralkylamino, alkoxyalkyl, hydroxy alkyl, cycloalkyl, phenyl lower alkyl or, lower alkyl, contains up to 7 carbon atoms and in other than cycloalkyl may be straight or branched. Such groups include methyl, ethyl, propyl, isopropyl, butyl, isobutyl, amyl, isoamyl, and the like.

The aryl group in aryl, aralkyl, aryl lower alkyline or aralkylamino is preferably phenyl or naphthyl.

The halo substituent is F, Cl, Br or I.

Where taken together with the nitrogen to which they are attached, H, lower alkyl, phenyl or phenyl lower alkyl in $R_2$ and $R_3$ form a heterocyclic ring, such as morpholino, pyrrolidino, piperidino, piperazino and the like.

The compounds of this invention may be readily prepared by art-recognized procedures from known starting materials and intermediates. The desired starting materials and intermediates can be prepared from readily available materials using standard organic reactions or alternatively, some starting materials and intermediates may be purchased from chemical supply companies.

For illustration, a schematic procedure for making a compound of the present invention follows:

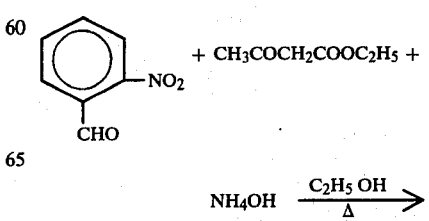

-continued

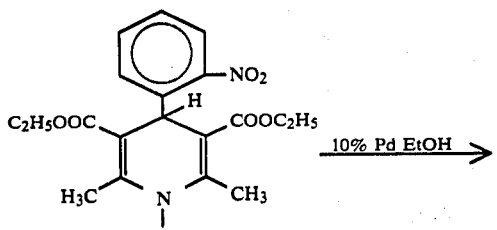

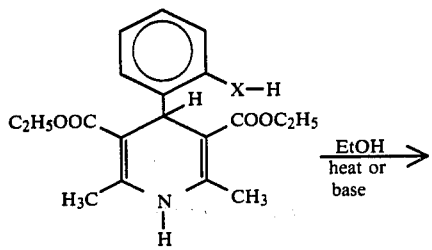

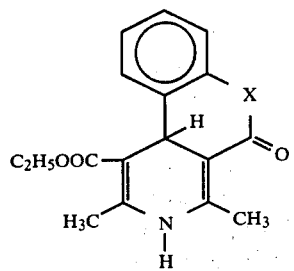

The compounds of this invention can also be prepared from N-substituted dihydropyridines (M is other than hydrogen) with proper substitution (—NH$_2$, OH, SH) by art-recognized ring closure reactions as illustrated in the examples.

The invention will be more fully illustrated in the examples that follow. These examples are given by way of illustration and are not to be considered as limiting.

EXAMPLE 1A

3-Benzyloxy-2-(hydroxymethyl)pyridine

Sodium hydroxide (31.5 grams, 0.78 mole) was dissolved in 100 ml water and 100 ml of acetone was added followed by 3-hydroxy-2(hydroxymethyl)pyridine hydrochloride (63.8 grams; 0.39 mole). 250 ml of acetone was added followed by benzyl bromide (74.1 grams; 51.5 ml; 0.43 mole). The mixture was refluxed for a period of 4.5 hours and the acetone evaporated in vacuo. The aqueous layer was extracted with CH$_2$Cl$_2$ (three times 150 ml) and the extracts dried (anhydrous Na$_2$SO$_4$) and concentrated to yield 88.1 grams of a brown liquid. The brown liquid (88.1 grams) was dissolved in ether and ether-HCl added to form the hydrochloride salt. The HCl salt was filtered and the filter cake dissolved in water. The aqueous solution was basified to afford a brown pasty precipate which on trituration with ether afforded 58.7 grams of material. Recrystallization from ethanol yielded 31.6 grams of a tan solid, m.p. 79°–80° C.

EXAMPLE 1B

3-Benzyloxy-2-formylpyridine

3-Benzyloxy-2-(hydroxymethyl)pyridine (35.1 grams; 0.16 mole) was dissolved in 1 liter of CHCl$_3$. Manganese dioxide (174 grams; 2.0 moles) was added and the mixture refluxed for a period of five hours. The reaction mixture was filtered hot through celite, and the solvent removed from the filtrate to afford a brown liquid weighing 23.5 grams.

EXAMPLE 1C

Diethyl 1,4-dihydro-4-(3-benzyloxypyridyl)-2,6-dimethyl 3,5-pyridine dicarboxylate 3-Benzyloxy-2-formylpyridine (23.5 grams; 0.11 mole), acetoacetic ester (28.6 grams; 28 ml; 0.22 mole) and ammonium hydroxide (35 ml) were dissolved in 200 ml ethanol and the clear solution (a white precipitate formed as refluxing began) refluxed for a period of 16 hours. The reaction mixture was cooled in ice, vacuum filtered, and the filtrate poured into ice and water. The product obtained was filtered, washed with water and dried. 21.7 grams of material was obtained (43%), m.p. 198°–201° C.

EXAMPLE 1D

Diethyl 1,4-dihydro-4-(3-hydroxypyridyl)-2,6-dimethyl-3,5-pyridine dicarboxylate Diethyl 1,4-dihydro-4-(3-benzyloxypyridyl)-2,6-dimethyl-3,5-pyridine dicarboxylate (7.0 grams; 0.016 mole) was hydrogenated in three batches using 1.2 grams of 10% Palladium on carbon. Material was dissolved in 300 ml ethanol and over a period of two hours there was a drop of 44 psi. The reaction mixtures were vacuum filtered through celite and the filtrate concentrated to approximately half the volume. Crystals formed on standing were filtered and collected. Recrystallization from acetonitrile yielded 6.2 grams of yellow crystals, m.p. 238°–239° C.

EXAMPLE 1E 8,10a-Dihydro-7,9-dimethyl-6-oxo-6H-pyrano(3,2-b:5,4-c') dipyridine-10-carboxylic acid ethyl ester Diethyl 1,4-dihydro-4-(3-hydroxypyridyl)-2,6-dimethyl-3,5-pyridine dicarboxylate (17.3 grams; 0.05 mole) was nearly dissolved in 250 ml toluene heated at 140° C. Diazabicyclo(5.4.0) undec-7-ene (8.3 grams; 8.2 ml; 0.05 mole) dissolved in 20 ml toluene was added and the reaction mixture refluxed for a period of 22 hours at 180° C. (bath temperature). The black solution was cooled and concentrated to afford 23.3 grams of a black paste. High pressure liquid chromatography (HPLC) using ethyl acetate yielded 8.3 grams of a yellow solid, m.p. 100°–150° C. Two recrystallizations from 2-propanol gave 4.5 grams (30%) of fluorescent yellow material, m.p. 150°–160° C.

EXAMPLE 2

7,9-Dimethyl-6-oxo-6N-pyrano[3,2-b:5,4-c']dipyridine-10-carboxylic acid ethyl ester 8,10a-Dihydro-7,9-dimethyl-6-oxo-6H-pyrano[3,2-b-5,4-c']dipyridine-10-carboxylic acid ethyl ester (7.2 g.; 0.024 mole) was dissolved in 170 ml acetic acid at 90° C. and sodium nitrate (9.9 g.; 0.14 mole) was added as a solid in small portions. The red mixture was heated on a steam bath for a period of 3 hours and then poured into ice. No crystallization occurred and the aqueous mixture was concentrated and then extracted with 250 ml CHCl₃, dried (anhydrous Na₂SO₄) and concentrated to afford 12.2 g. of brown flaky material. The material was triturated with approximately 450 ml hexane:acetone (6:4). The mixture was filtered and the filtrate was concentrated to yield 5.7 g. of a brown solid, m.p. 85° C. Crystallization from ethanol gave 1.2 g. of a light brown solid, m.p. 175°–180° C.

EXAMPLE 3A

Diethyl 1,4-dihydro-4-(2-nitrophenyl) 2,6-dimethyl-3,5-pyridine dicarboxylate O-Nitrobenzaldehyde (151.1 gms, 1.0 mole), acetoacetic ester (260.2 gms, 2.0 moles) and 320 ml ammonium hydroxide were combined in 700 ml ethanol and refluxed for a period of 24 hours. The reaction mixture was poured into 2 liters ice and water. The material solidified out on standing. The material was filtered washed with water and air dried. The crude dihydropyridine (162.0 gms) was crystallized from methanol to afford 98 gms (28%), m.p. 116°–119° C.

EXAMPLE 3B

Diethyl 1,4-dihydro-4-(2-aminophenyl)-2,6-dimethyl-3,5-pyridine dicarboxylate Diethyl 1,4-dihydro-4-(2-nitrophenyl)-2,6-dimethyl-3,5-pyridine dicarboxylate (57.4 gms, 0.15 mole) was dissolved in 500 ml ethanol and hydrogenated (Parr) with 4.0 gms of 10% Pd on carbon over a period of 24 hours. The catalyst was filtered through Celite, and the filtrate concentrated to yield 28.0 gms of the crude aminodihydropyridine. Two recrystallizations from acetonitrile afforded 13.8 gms of the pure product (25%), m.p. 137°–139° C.

EXAMPLE 3C

3,5,6,10b-Tetrahydro-2,4-dimethyl-5-oxo-benzo[c][2,7-]naphthyridine-1-carboxylic acid ethyl ester Diethyl 1,4-dihydro-4-(2-aminophenyl)-2,6-dimethyl-3,5-pyridine dicarboxylate (90.0 gms., 0.26 mole) was dissolved in 250 ml dry DMF and the solution refluxed for a period of 72 hours. The solvent was removed under vacuum and the residue recrystallized twice from ethyl acetate to afford 5.4 gms (7%), m.p. 236°–238° C.

EXAMPLE 4A

2-Benzyloxybenzaldehyde

Sodium hydroxide (20.0 gms.; 0.5 mole) was dissolved in 150 ml H₂O and salicylaldehyde (53.2 ml; 0.5 mole) dissolved in 200 ml acetone was added, followed by benzyl bromide (65.4 ml; 0.55 mole) dissolved in 200 ml acetone. The reaction mixture was refluxed for a period of 24 hours and allowed to cool. The acetone was evaporated in vacuum and the two phase residue extracted with 300 ml CH₂Cl₂. The CH₂Cl₂ layer was washed with 150 ml H₂O and dried over anhydrous Na₂SO₄. The Na₂SO₄ was filtered off and the solvent removed from the filtrate to yield 141 grams of the crude product.

EXAMPLE 4B

Diethyl 1,4-dihydro-4-(2-benzyloxyphenyl)-2,6-dimethyl-3,5-pyridine dicarboxylate Crude 2-benzyloxybenzaldehyde (70 gms.; 0.33 mole) acetoacetic ester (85.8 gms.; 0.66 mole) and ammonium hydroxide (80 ml) were dissolved in 200 ml ethanol, and the clear yellow solution refluxed for a period of 24 hours. The solution was then poured into ice water and the brown oily material was crystallized twice from ethanol to afford 22.6 grams (17%) of material, m.p. 134°–136° C.

EXAMPLE 4C

Diethyl 1,4-dihydro-4-(2-hydroxyphenyl)-2,6-dimethyl-3,5-pyridine dicarboxylate Diethyl 1,4-dihydro-4-(2-benzyloxyphenyl)-2,6-dimethyl-3,5-pyridine dicarboxylate (13.3 grams, 0.03 mole) was dissolved in 250 ml ethanol, 1.5 grams of 10% palladium on carbon was added and the reaction mixture reduced on a Parr Hydrogenator. A drop of 111 psi was noted over a period of seven hours. The Pd-C was filtered off, the solvent removed from the filtrate. Two recrystallizations from acetonitrile yielded 3.4 grams (34%) of the desired product, m.p. 159°–161° C.

EXAMPLE 4D

3,10b-Dihydro-2,4-dimethyl-5-oxo-5H[1]benzopyrano[3,4-c]pyridine-1-carboxylic acid ethyl ester Diethyl 1,4-dihydro-4-(2-hydroxyphenyl)-2,6-dimethyl-3,5-pyridine dicarboxylate (3.4 grams, 0.01 mole) was dissolved in 50 ml toluene at 70°–80° C. 1,8-Diazabicyclo[5.4.0] undec-7-ene (DBU) (1.52 grams, 0.01 mole) was added and the solution refluxed for a period of 22 hours (bath temperature: 180° C.) and allowed to cool. The yellow solution was then concentrated to red oil, wt.: 5 grams. High pressure liquid chromatography using CHCl₃ yielded 2.3 grams of material as a yellow solid. Trituration with hot hexane yielded a yellowish solid, m.p. 125°–135° C. Recrystallization from acetonitrile afforded 1.3 grams, m.p. 144°–146° C.

EXAMPLE 5

2,4-Dimethyl-5-oxo-5H[1]-benzopyrano[3,4-c]pyridine-1-carboxylic acid ethyl ester 3,10b Dihydro-2,4-dimethyl-5-oxo-5H[1]benzopyrano[3,4-c]pyridine-1-carboxylic acid ethyl ester (10.2 grams, 0.034 mole) was dissolved in 250 ml acetic acid at 90° C. on a water bath and sodium nitrite (14.1 grams, 0.2 mole) was added in small portions as a solid. The mixture was heated on the steam bath for three hours and poured into ice-water. The mixture was vacuum filtered leaving an orange residue (2.1 grams). The filtrate was concentrated and the residue partitioned between chloroform and water. The chloroform layer was washed once with H₂O, dried (anhydrous Na₂SO₄) and concentrated to afford a brown paste weighing 7.9 grams. The material was triturated with hexane-acetone (3.2), followed by ethyl acetate. The red brown paste (6.7 grams) was recrystallized twice from acetonitrile to yield light-orange crystals, 2.0 grams, m.p. 125°–128° C.

Compounds of the present invention exhibited potent activity as measured by the in-vitro antigen-induced histamine release test, the description of which follows.

Cyclic Nucleotide Phosphodiesterase (cNUC-PDE) Assay: CNUC-PDE was measured by a modification of the one-step procedure described by Thompson et al. (1979). The reaction was carried out in 7 ml scintillation vials. The reaction mixture consisted of 5 mM MgCl₂., 50 mM tris-(hydroxymethyl)aminomethane buffered to pH 8.0 at 37° C. with hydrochloric acid (Tris-chloride), $1-2\times10^5$ cpm $^3$H-labeled cyclic nucleotide substrate, appropriate concentration of non-labeled cyclic nucleotide, 25 μg/ml lyophilized *Ophiophagus hannah* venom and appropriate enzyme for linear reaction conditions. The timed reactions were initiated by the addition of an enzyme, incubated at 37° C. for appropriate times for linear reaction rates, and stopped with the addition of 0.8 ml of 50% (v/v) AG 1×8 (200–400 mesh) ion-exchange resin in 50% (v/v) ethanol-Tris-acetate buffer (pH 8.0). The vials were vortexed and the resin mixture allowed to equilibrate for 15 min at 4° C. Scintillation fluid (4.5 ml) was added and radioactivity quantitated in a liquid scintillation counter.

Dog Heart Enzyme Preparations: Mongrel dogs were overdosed with Nembutal ® and their hearts surgically removed. The ventricular muscle was dissected out, rinsed in 0.9% (w/v) saline, and cut into large pieces. These pieces were blended with a Waring Blender for 45 seconds in 4 ml of 50 mM Tris-chloride (pH 8.0, 4° C.) per gram weight of tissue. The homogenate was strained through cheesecloth and then centrifuged at 400× g for 2 min at 4° C. The resulting supernatant was then centrifuged at 105,000× g for 1 h. The high speed supernatant was decanted, aliquoted and stored at −80° C. The high-speed pellet was resuspended in a volume of buffer equal to the supernatant and gently re-homogenized with a motor driven teflon pestle and a glass barrel. This homogenate was recentrifuged at 105,000× g for 1 h. The washed pellet was resuspended in buffer at 2 times the volume of original supernatant and gently rehomogenized to evenly dispurse the pellet. The resuspended pellet was then aliquoted and stored at −80° C.

Mast Cell Enzyme Preparations: Peritoneal cells were collected and mast cells purified by a procedure similar to that described by Yurt et al., (1977). For each experiment 10–15 male rats (Charles River Spraque Dawley, 200–300 g) were sacrificed by decapitation. The abdominal fur was shaved off and 10 ml of isolation buffer (see below) containing 10% fetal calf serum (FSC) was injected i.p. into each rat. The abdomen was gently massaged. The peritoneal cavity was surgically exposed and the injected buffer removed with a pasteur pipette. This exudate was centrifuged at 100× g for 2 minutes. The supernatant was discarded and the cells gently resuspended in isolation buffer. This centrifugation-resuspension procedure was done 2 times. The cells were finally suspended in a total of 6 ml isolation buffer containing 10% FCS. Each 1 ml of cell suspension (8–12% mast cells) was layered over 2 ml of 25% (w/v) Metrizamide ® in isolation buffer (no FCS, refractive index=1.3725). After 15 min centrifugation at 100× g, the upper layer of isolation buffer, the interface and upper ⅓ of the Metrizamide ® layer were all removed and discarded. The side of the centrifuge tube was wiped clean, 10 ml of isolation buffer containing 10% FCS added, and the cellular pellet gently resuspended. This cell suspension was centrifuged for 10 min at 1000× g and the resulting supernatant discarded. The cellular pellet was resuspended in a small volume of isolation buffer containing 10% FCS. The cells (<80% mast cells) were counted with a haemocytometer. Just prior to the enzyme assay, the cell suspension was centrifuged for 10 min at 1000× g and the cells resuspended in an appropriate volume of assay buffer (ca. $2\times10^6$ cells/ml). The cells were lysed by sonication (30 sec at a setting of 2 with a Branson Sonifer Microprobe).

The isolation buffer consisted of 150 mM NaCl, 2.7 mM KCl, 0.1 mM ethylene-glycol-bis-(β-aminoethyl ether)-tetra acetic acid (EGTA), 0.1% gelatin, 1 mM sodium phosphate buffered to pH 7.0 at 4° C. Buffer containing FCS was 10% by volume FCS and 90% isolation buffer. Assay buffer was 40 mM Tris-Cl, pH 8.0 at 37° C.

Testing of Compounds: Compounds were normally dissolved in 100% ethanol and then diluted with assay buffer to make a 400 μM solution containing 8% ethanol. This intermediate solution was aliquoted appropriately to assay tubes for the desired final concentration of compound and a maximum of 2% ethanol. All compounds were initially tested at 100 μM and retested if there was more than 30% inhibition of any test parameter. If greater than 60% inhibition of any parameter was obtained, compounds were tested at several concentrations to obtain an $I_{50}$ value (i.e., the concentration causing 50% inhibition). With rat mast cell homogenates, hydrolysis was measured with 0.5 μM adenosine-3′,5′-monophosphate (cyclic AMP) and 0.5 μM guanosine-3′,5′-monophosphate (cyclic GMP).

The activity of a compound is expressed as % inhibition of net antigen-induced histamine release. In the case of an active compound the concentration of the compound required for 50% inhibition for AIR ($I_{50}$) is determined.

Representative results, obtained according to the above-described procedure, for 3,5,6,10b-tetrahydro-2,4-dimethyl-5-oxo-benzo[c][2,7] naphthyridine-1-carboxylic acid ethyl ester are <60% PDE inhibition and <50% guinea pig lung inhibition.

In spontaneously hypertensive [SHR] rats (as described in Laffan, R. J., Patterson, A., Hitch, S. W., Jeunelot, Technique for Prolonged Continuous Recording of Blood Pressures of Unrestricted Rats, Cardiovascular Research, Vol. 6, pp. 319–24, 1972),3,10b-dihydro-2,4-dimethyl-5-oxo-5H[1]benzopyrano[3,4-C]pyridine-1-carboxylic acid ethyl ester (Example 4D) administered intraperitoneal (ip) dose of 100 mg/Kg reduced blood pressure by 17–22% over 2 hours duration.

The therapeutic compounds of the present invention may be administered alone or in combination with pharmaceutically acceptable carriers, the proportion of which is determined by the solubility and chemical nature of the compound, chosen route of administration and standard pharmaceutical practice.

The physician will determine the dosage of the present therapeutic compounds which will be most suitable and it will vary with the form of administration and the particular compound chosen, and furthermore, it will vary with the particular patient under treatment. He will generally wish to initiate treatment with small dosages substantially less than the optimum dose of the compound and increase the dosage by small increments until the optimum effect under the circumstances is reached. It will generally be found that when the composition is administered orally, larger quantities of the active agent will be required to produce the same effect as a smaller quantity given parenterally. The compounds are useful in the same manner as other anti-asthma agents and the dosage level is of the same order of magnitude as is generally employed with these other therapeutic agents. The therapeutic dosage will generally be from 10 to 750 milligrams per day and higher although it may be administered in several different dosage units.

What is claimed is:

1. A compound of the structure:

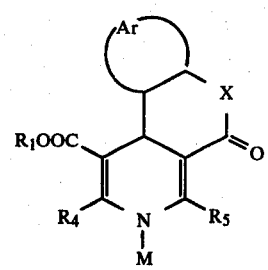

and pharmaceutically acceptable salts thereof, wherein:

Ar is phenyl, naphthyl, heteroaryl, and phenyl mono- or disubstituted by halo, $CF_3$, $NO_2$, COOH, COOR, CN, lower alkyl S, lower alkyl SO, lower alkyl $SO_2$, $OCF_3$, $SCF_3$, $OC\equiv CH$, $OCH_2CH=CH_2$, $CONH_2$, $=C=CH-$ lower alkyl, lower aralkyl, styrryl, lower cycloalkyl having 5 to 7 carbons;

X is S, NH, O, or N—R;

$R_1$ is H, lower alkyl, aralkyl, aminoalkyl, dialkylamino, aralkylamino, phenylthio, phenyl sulfoxide, phenyl sulfone, alkoxyalkyl, hydroxyalkyl, alkenyl, cycloalkyl or aryl;

$R_4$ and $R_5$ are independently lower alkyl, formyl, CN, $CH_2OH$, dialkylaminomethyl, dialkylaminoethyl,

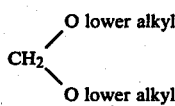

aryl, aryl lower alkyl,

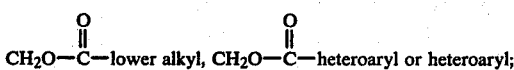

M is H, alkyl, aryl, alkoxy, $(CH_2)_nCOOR$,

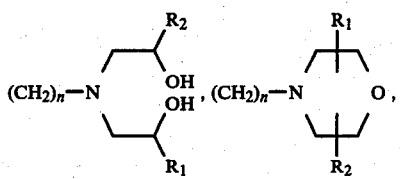

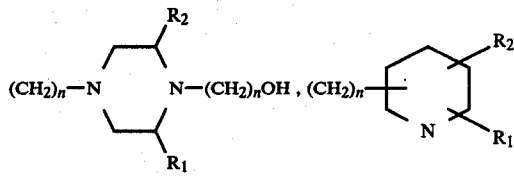

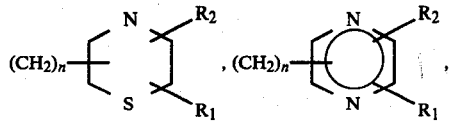

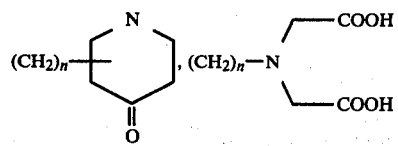

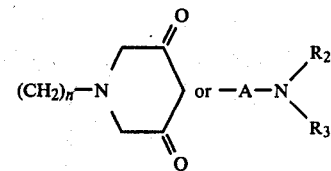

wherein

A is $C_2$ to $C_4$ alkyl and may be branched or straight,

R is H or lower alkyl, $R_2$ and $R_3$ are independently H, lower alkyl, phenyl or phenyl lower alkyl and when taken together with the nitrogen to which they are attached form a heterocylic ring, and n is 0–2 inclusive.

2. The compound of claim 1 wherein the alkyl group in aralkyl, aminoalkyl, aralkylamino, alkoxyalkyl, hydroxyalkyl, cycloalkyl, lower alkyl and phenyl lower alkyl contains up to 7 carbon atoms.

3. The compound of claim 1 wherein the alkyl group in aralkyl, aminoalkyl, aralkylamino, alkoxyalkyl, hydroxyalkyl, lower alkyl and phenyl lower alkyl is a straight chain.

4. The compound of claim 1 wherein the alkyl group in aralkyl, aminoalkyl, aralkylamino, alkoxyalkyl, hydroxyalkyl, lower alkyl, and phenyl lower alkyl is a branched chain.

5. The compound of claim 1 wherein the alkyl group in aralkyl, aminoalkyl, aralkylamino, alkoxyalkyl, hydroxyalkyl, lower alkyl and phenyl lower alkyl is methyl, ethyl, propyl, isopropyl, butyl, isobutyl, amyl or isoamyl.

6. The compound of claim 1 wherein the aryl group in aryl, aralkyl, aryl lower alkyline, and arylalkylamino is phenyl or naphthyl.

7. The compound of claim 1 wherein said halo is F, Cl, BR or I.

8. The compound of claim 1 wherein said heterocyclic ring is morpholino, pyrrolidino, piperidino or piperazino.

9. The antihypertensive compound of 3,10b-dihydro-2,4 dimethyl-5-oxo-5H[1]benzo-pyrano[3,4-C]pyridine-1-carboxylic acid ethyl ester.

10. A therapeutic composition for the treatment of asthma comprising: an effective amount of a member selected from the compounds having the structure:

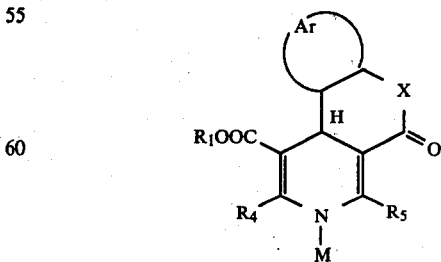

and pharmaceutically acceptable salts thereof, wherein:

Ar is phenyl, naphthyl, heteroaryl, and phenyl mono- or disubstituted by halo, $CF_3$, $NO_2$, COOH, COOR, CN, lower alkyl S, lower alkyl SO, lower alkyl SO₂, OCF₃, SCF₃, OC—CH, OCH₂CH=CH₂, CONH₂, =C=CH— lower alkyl, lower aralkyl, styrryl, lower cycloalkyl having 5 to 7 carbons;

X is S, NH, O, or N—R;

R₁ is H, lower alkyl, aralkyl, amino alkyl, dialkylamino, aralkylamino, phenylthio, phenyl sulfoxide, phenyl sulfone, alkoxyalkyl, hydroxy alkyl, alkenyl, cycloalkyl or aryl;

R₄ and R₅ are independently lower alkyl, formyl, CN, CH₂OH, dialkylaminomethyl, dialkylaminoethyl,

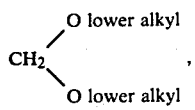

aryl, aryl lower alkyl,

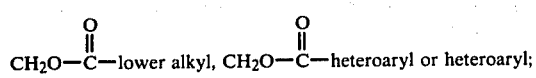

M is H, alkyl, aryl, alkoxy, (CH₂)ₙCOOR,

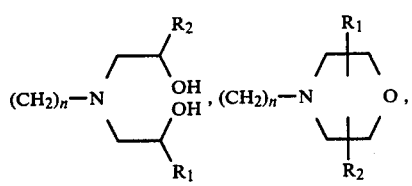

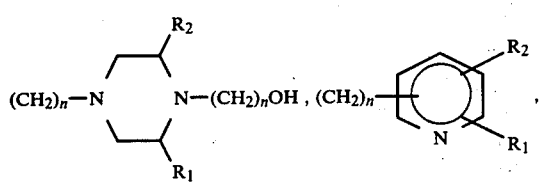

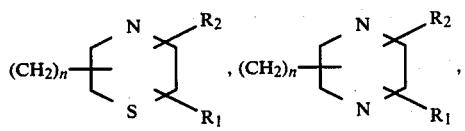

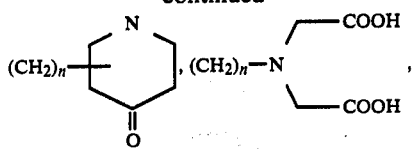

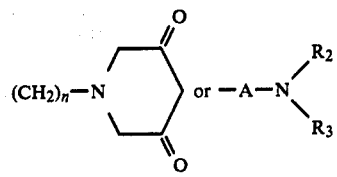

A is C₂ to C₄ alkyl and may be branched or straight, R is H or lower alkyl, R₂ and R₃ are independently H, lower alkyl, phenyl or phenyl lower alkyl and when taken together with the nitrogen to which they are attached form a heterocyclic ring, and n is 0-2 inclusive; and a pharmaceutically acceptable carrier.

11. The therapeutic composition of claim 10 wherein the alkyl group in aralkyl, aminoalkyl, aralkylamino, alkoxyalkyl, hydroxyalkyl, cycloalkyl, lower alkyl and phenyl lower alkyl contains up to 7 carbon atoms.

12. The therapeutic composition of claim 10 wherein the alkyl group in aralkyl, aminoalkyl, aralkylamino, alkoxyalkyl, hydroxyalkyl, lower alkyl and phenyl lower alkyl is a straight chain.

13. The therapeutic composition of claim 10 wherein the alkyl group in aralkyl, aminoalkyl, aralkylamino, alkoxyalkyl, hydroxyalkyl, lower alkyl and phenyl lower alkyl is a branched chain.

14. The therapeutic composition of claim 10 wherein the alkyl group in aralkyl, aminoalkyl, aralkylamino, alkoxyalkyl, hydroxyalkyl, lower alkyl and phenyl lower alkyl is methyl, ethyl, propyl, isopropyl, butyl, isobutyl, amyl or isoamyl.

15. The therapeutic composition of claim 10 wherein the aryl group in aryl, aralkyl, aryl lower alkyline, and arylalkylamino is phenyl or naphthyl.

16. The therapeutic composition of claim 10 wherein said halo is F, Cl, Br or I.

17. The therapeutic composition of claim 10 wherein said heterocyclic ring is morpholino, pyrrolidino, piperidino or piperazino.

18. A method of inhibiting histamine release in a mammal by administering to said mammal an effective amount of a composition of claim 10.

* * * * *